(12) United States Patent
Bock

(10) Patent No.: US 10,028,760 B2
(45) Date of Patent: Jul. 24, 2018

(54) HIGH INTENSITY ULTRASONIC TONGUE CLEANER

(71) Applicant: Robert T. Bock, Brewster, NY (US)

(72) Inventor: Robert T. Bock, Brewster, NY (US)

(73) Assignee: ROBERT T. BOCK CONSULTANCY LLC, Brewster, NY (US)

(*) Notice: Subject to any disclaimer, the term of this patent is extended or adjusted under 35 U.S.C. 154(b) by 378 days.

(21) Appl. No.: 14/821,721

(22) Filed: Aug. 8, 2015

(65) Prior Publication Data

US 2016/0051271 A1 Feb. 25, 2016

Related U.S. Application Data

(60) Provisional application No. 62/040,034, filed on Aug. 21, 2014.

(51) Int. Cl.
*A61B 17/24* (2006.01)
*A61N 7/00* (2006.01)
*A61B 17/00* (2006.01)

(52) U.S. Cl.
CPC .............. *A61B 17/244* (2013.01); *A61N 7/00* (2013.01); *A61B 2017/00141* (2013.01); *A61B 2017/00402* (2013.01); *A61B 2017/00415* (2013.01); *A61B 2017/00734* (2013.01); *A61B 2017/00889* (2013.01)

(58) Field of Classification Search
CPC ........ A61B 17/244; A61B 2017/00415; A61B 2017/00402; A61B 2017/00889; A61B 2017/00141; A61N 7/00
See application file for complete search history.

(56) References Cited

U.S. PATENT DOCUMENTS

| 1,893,524 | A | | 1/1933 | Shanley |
| 5,138,733 | A | * | 8/1992 | Bock .................. A46B 7/04 15/167.1 |
| 5,369,831 | A | * | 12/1994 | Bock .................. A46B 7/04 15/167.1 |

(Continued)

FOREIGN PATENT DOCUMENTS

| WO | WO 2002/034145 | 5/2002 |
| WO | WO 2014/004979 A1 | 1/2014 |

OTHER PUBLICATIONS

"Megasonex—The Ultrasound Tongue Scraper," Mar. 12-16, 2013, koelnmesse NDP Products, Cologne, Germany (http://neuheiten.koelnmesse.net/200/2013/us/products/view/product_id:11048/cat:13531—downloaded Aug. 16, 2016).†

*Primary Examiner* — Son Dang

(57) ABSTRACT

An ultrasonic tongue cleaner applying high intensity non-attenuated ultrasound pressure waves to the tongue concurrently with the mechanical scraping action is disclosed. The ultrasound component is operative to damage and deactivate odor causing bacterial chains on the surface and in the folds of the tongue. A silver based antimicrobial attachment further enhances the performance of the tongue cleaner. Various configurations are disclosed, including user removable and replaceable tongue cleaner heads with and without antimicrobial silver. A motorized version featuring sonic frequency orbital vibration of the tongue cleaner head is described.

8 Claims, 3 Drawing Sheets

(56) References Cited

U.S. PATENT DOCUMENTS

| | | | | |
|---|---|---|---|---|
| 5,496,256 A * | 3/1996 | Bock | A61C 8/00 433/174 |
| 5,546,624 A * | 8/1996 | Bock | A46B 7/04 15/167.1 |
| 5,827,064 A * | 10/1998 | Bock | A61C 17/20 433/216 |
| 5,980,541 A | 11/1999 | Tenzer | |
| 6,363,949 B1 | 4/2002 | Brown | |
| 6,951,567 B2 | 10/2005 | Levit | |
| 7,478,452 B2 * | 1/2009 | Rosenblood | A61B 17/24 15/111 |
| 9,320,580 B2 * | 4/2016 | Montgomery | A61C 19/066 |
| 2003/0170453 A1 * | 9/2003 | Foss | A01N 57/16 428/373 |
| 2006/0141015 A1 * | 6/2006 | Tessier | A01N 59/16 424/443 |
| 2007/0119969 A1 * | 5/2007 | Collins, Jr. | A61M 11/005 239/102.1 |
| 2008/0060148 A1 * | 3/2008 | Pinyayev | A61B 5/0088 15/22.1 |
| 2008/0276393 A1 * | 11/2008 | Russell | A46B 7/00 15/105 |
| 2008/0313828 A1 * | 12/2008 | Grez | A61C 17/20 15/22.1 |
| 2009/0131960 A1 * | 5/2009 | Tanaka | A61B 17/244 606/161 |
| 2009/0211041 A1 * | 8/2009 | Bock | A46B 13/023 15/22.1 |
| 2009/0211042 A1 * | 8/2009 | Bock | A46B 13/023 15/22.1 |
| 2009/0212133 A1 * | 8/2009 | Collins, Jr. | A61M 11/005 239/338 |
| 2010/0133162 A1 * | 6/2010 | Huang | F24F 6/12 210/206 |
| 2011/0065063 A1 * | 3/2011 | Bock | A61C 1/14 433/118 |
| 2011/0289702 A1 * | 12/2011 | Lee | A61C 17/26 15/22.1 |
| 2011/0289707 A1 * | 12/2011 | Schaefer | A46B 15/0002 15/105 |
| 2012/0137453 A1 * | 6/2012 | Tsukino | A61C 17/20 15/22.1 |
| 2014/0261538 A1 * | 9/2014 | Elseri | A46B 9/005 134/6 |
| 2014/0298605 A1 * | 10/2014 | Ivory | A46B 15/0081 15/111 |
| 2015/0182240 A1 * | 7/2015 | Wawiluk | A61B 17/24 606/161 |
| 2015/0313993 A1 * | 11/2015 | Bock | A61M 37/0092 604/22 |
| 2015/0327964 A1 * | 11/2015 | Bock | A61C 17/20 433/216 |
| 2016/0206412 A1 * | 7/2016 | Bock | A46B 15/0028 |

\* cited by examiner
† cited by third party

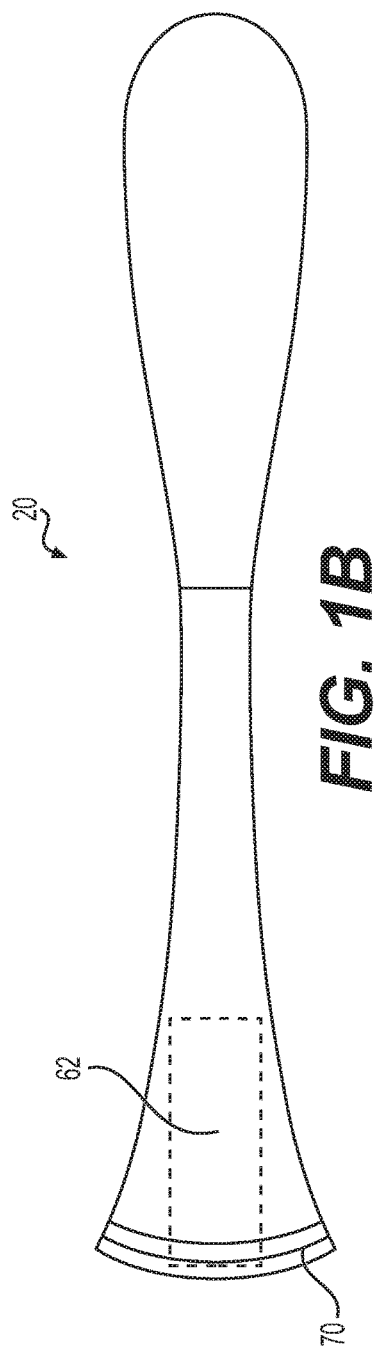
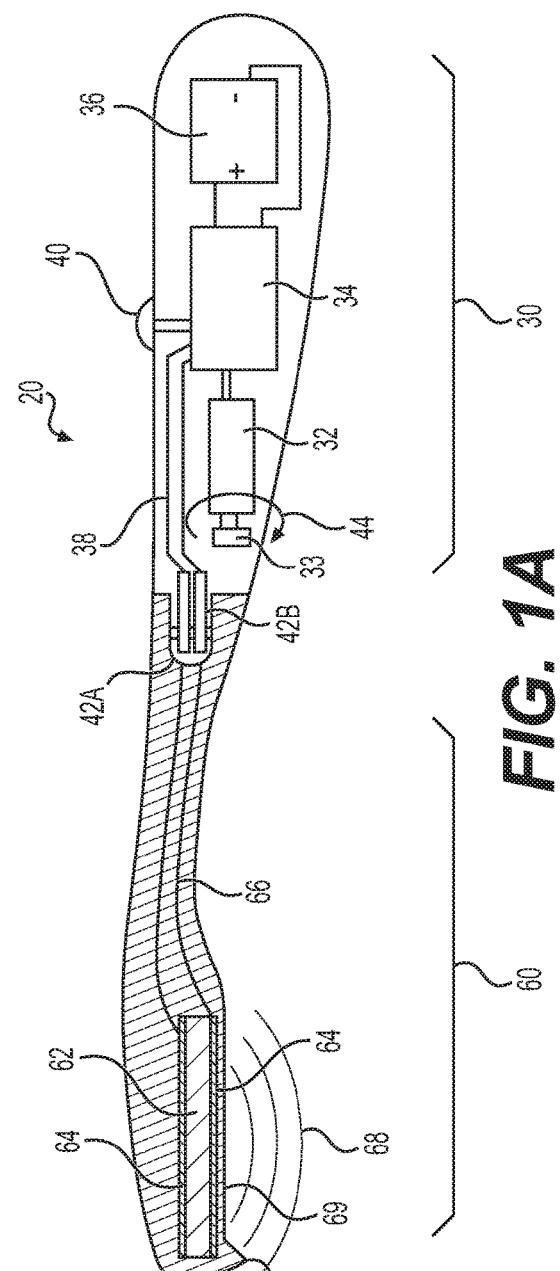

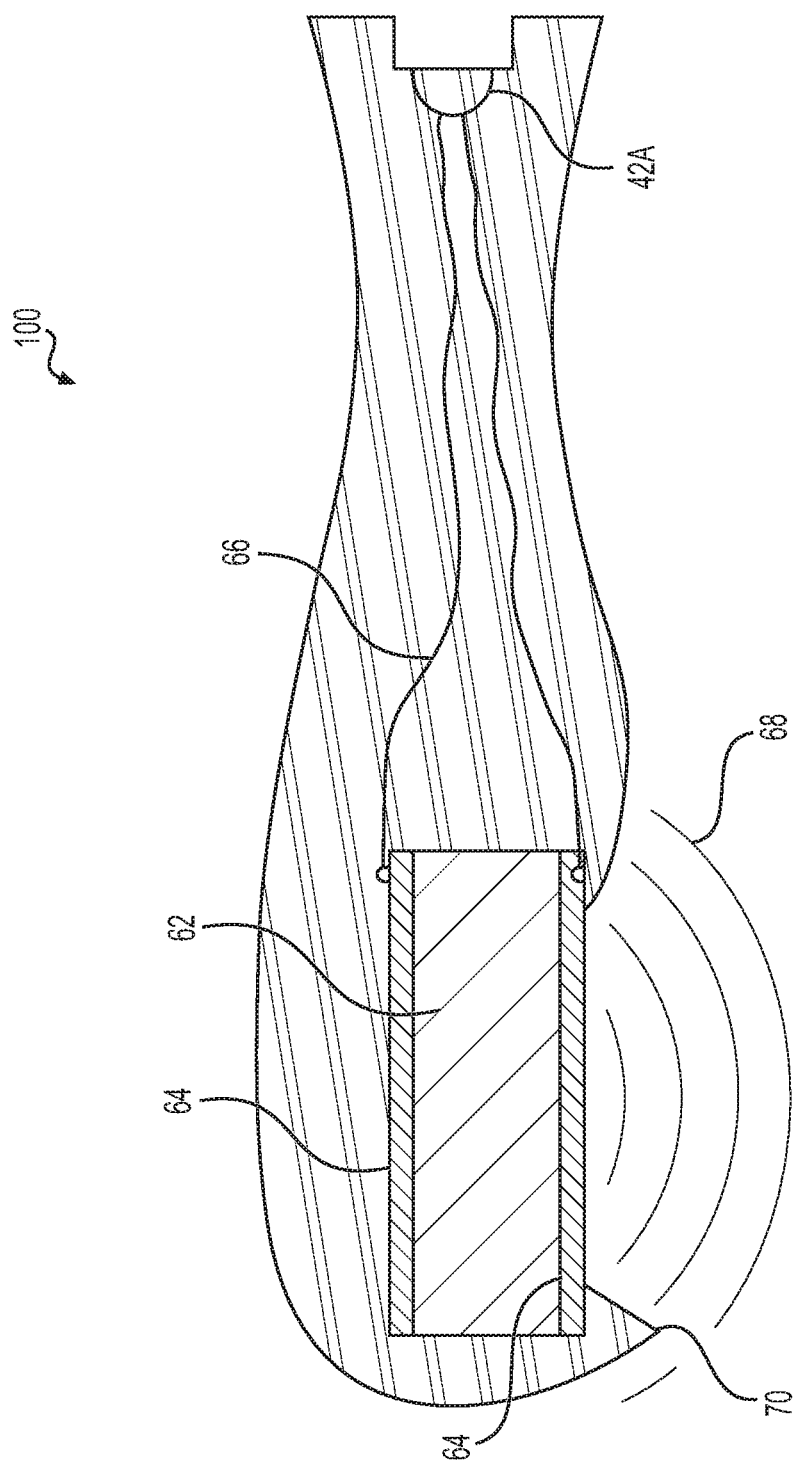

HIGH INTENSITY ULTRASONIC TONGUE CLEANER

BACKGROUND OF THE INVENTION

1. Field of the Invention

This invention relates to tongue scrapers and more particularly tongue scrapers utilizing sonic and ultrasonic acoustic mechanism to increase the effectiveness of the tongue scrapers and to provide for enhanced oral hygiene.

2. Description of Prior Art

The early tongue scrapers were invented in France in the 1930s (0399946-5/1932) to reduce bad breath. Various other tongue scrapers followed, such as U.S. Pat. No. 1,893,524 by Shanley, and U.S. Pat. No. 6,951,567 B2 by Levit, and many others. Many other devices followed wherein the tongue scraper part appeared in combination with manual toothbrushes (U.S. Pat. No. 5,980,541 by Tenzer) and (U.S. Pat. No. 7,478,452 B2 by Rosenblood et al.), and in combination with a dental floss dispenser (U.S. Pat. No. 6,363,949 B1 by Brown). All of these devices were developed for the common theme, for scraping and removing odor causing undesirable matter from the surface of the tongue. The odor causing undesirable matter (debris) is typically composed of enzymes, proteins, sugars, plaque, and anaerobic bacteria. These materials exist on the top surface of the tongue and in the bottom of the cavities between the papillae. As these materials decompose, the decomposition process results in sulfur gas, which is the cause of bad breath.

An improved attempt is represented by WO2002034145, which discloses a tongue scraper, which is connected to an ultrasonic dental device typically used for removing hard calcified tartar from teeth in the dental office. While this combination device improves the effectiveness of the tongue scraper by adding a low amplitude ultrasonic frequency vibration to the tongue scraper, it can only be used in the dental office and it is not practical for daily home use.

An Ultrasonic Tongue Scraper, WO2014/004979A1 is proposed by Wawiluk, which is designed for home use. In the specifications of his disclosure Wawiluk proposes a structure comprised by a Tongue Scraper Head Portion 100 and a Body Portion 200, wherein the Body Portion 200 comprises an ultrasound generator configured to generate ultrasound. The ultrasound generator is neither further defined in the specifications nor shown in the drawings of WO2014/004979A1. Not defining the structure of the proposed ultrasound generator and not defining how the generated ultrasound is transmitted from the Body Portion 200 to the Tongue Scraper Head Portion 100 is a critical failure of this proposal to teach the art.

It is not obvious of how and if the ultrasound generated in the Body Portion 200 is transferred to the ultrasound application part Leading Edge 105 of the Tongue Scraper Head Portion 100 of the invention.

What is clear is that the ultrasound generated in the Body Portion 200 has to progress through large amount of structural attenuation, multiple ultrasound attenuating surface interfaces and ultrasound killing air gaps to arrive to the surface of the Leading Edge 105 which is used to contact the tongue and supposed to transmit ultrasound from the device to the tongue, to assist the manual scraping. Therefore, it is clear that in all of the proposed embodiments described in the specifications of WO2014/004979A1 the ultrasound reaching the working Leading Edge 105 is highly limited in intensity and efficacy.

The teachings of the early art of how the debris is scraped off from the top surface of the tongue is well defined. However, scraping the debris off from the top surface of the tongue only reduces the malodor from the sulfur gases generated by the decomposing matter on the top surface of the tongue, and does this only temporarily. It does not impact proteins, sugars, plaque and the anaerobic bacteria in the folds of the tongue and in the creases of the papillae. To render these hidden bacteria ineffective, and to stop the sulfur gas producing decomposition process, intense ultrasonic pressure waves are required to penetrate to the bottom of the folds in the tongue and the cavities of the papillae. None of the prior art disclosed teach this.

While there was progress to date toward an effective tongue cleaner device to eliminate bad mouth odor, the past progress is only a temporary and momentary solution. The quest for a permanent solution to eliminate or render ineffective the root cause of the malodor, the anaerobic bacteria from the tongue and the papillae is still not fulfilled.

SUMMARY OF THE INVENTION

Responding to the above described needs; the goals of this invention are to provide methods and devices, which in addition to removing the sulfur gas producing decomposing debris from the top of the tongue, also effectively neutralize or render ineffective the anaerobic bacteria hiding in the folds of the tongue and in the papillae and to stop the sulfur gas producing decomposition of the residual hidden matters such as enzymes, proteins, sugars, plaque, and other matters.

The invention achieves these goals by the development and disclosure of a new Improved Intensity Ultrasonic Tongue Scraper employing a high efficiency non-attenuated novel ultrasound transducer system wherein the transducer resides in the tongue scraper head irradiating the tongue through a ¼ wavelength matching layer and the scraping edges of the tongue scraper. The present invention eliminates all of the numerous ultrasound attenuating surface interfaces and ultrasound-stopping air gaps between the ultrasound transducer, the handle body portion, the stem of the body portion, the head portion, and the leading (scraping) edge of the prior art.

The invention also incorporates silver as an electrical contact surface on the ultrasound transducer. The antimicrobial properties of silver have been known in the science for many centuries. Silver is known to inhibit bacterial growth and to deactivate proteins and enzymes. Silver nanoparticles have been heavily studied and proven as antimicrobial materials. Their simple synthesis and highly effective observed antibacterial activity make them a very attractive form of silver administration from the exposed silver contact surface of the ultrasound transducer.

Following this summary, two preferred embodiments of the invention are described in details. In one of the embodiments a ¼ wavelength ultrasound-matching layer is utilized between the transducer and the tongue, enhancing the transmission and coupling of the non-attenuated ultrasound energy to the tissue of the tongue. In the second embodiment the transducer's silver contact surface is exposed to be in intimate contact with the tongue.

The user operates the invention by manual motion to scrape off the debris from the tongue and to irradiate the various areas of tongue with ultrasound. Some embodiments apply antimicrobial silver to the tongue in combination with the ultrasonic pressure waves. In certain other embodiments a sonic frequency motion of the tongue scraper head augments the manual motion of the user.

All embodiments utilize the new method to subject the anaerobic bacteria in the folds of the tongue and papillae to ultrasonic pressure waves between 20 kHz and 20 MHz frequency, more typically within 750 kHz and 2 MHz frequency, at a non-attenuated intensity from 0.02 to 0.5 W/cm$^2$, more typically within 0.035 to 0.150 W/cm$^2$ either concurrently, in conjunction with, or independently of the manual motion or sonic frequency vibration of the device.

Accordingly, the new Improved Intensity Ultrasonic Tongue Scraper invention comprises a handle portion and a tongue scraper head portion. The tongue scraper head portion comprises one or more ultrasound transducers and one or more scraping edges. The tongue scraper head portion is typically removable from the handle portion and replaceable when worn out. In a removable configuration various size heads can be attached to the handle, sometimes having various performance features. A non-removable configuration would allow a lower cost and simpler disposable system. The handle portion contains a battery pack, an electronic motor to generate sonic frequency tactile vibrations of the tongue scraper head portion, an electronic control module to generate the ultrasonic frequency current to energize the ultrasound transducer(s) in the tongue scraper head portion and to provide control of the other functions in the tongue scraper such as motor speed control, and battery charge control. The tongue scraper system may also include a battery charging stand to provide the primary current for charging the battery in the handle, usually by conductive current means.

The direct exposure of the transducer to the tongue completely eliminates all structural attenuation of the ultrasound energy of the prior art, and provides non-attenuated high intensity ultrasound pressure waves to irradiate the tongue.

The ultrasound transducer located in the tongue scraper head in direct contact with the tongue with or without a ¼ wavelength ultrasound-matching layer is one of the major inventive steps of the invention.

Another inventive step of this invention is to expose the silver contact surface of the ultrasound transducer, in close proximity of the scraping edge of the instrument, to the surface of the tongue. In this embodiment not only that the silver contacts the surface of the tongue, but as the scraping edge is being drawn across the tongue surface it opens up the folds in the tongue surface and the papillae to allow the silver to contact and interact with the enzymes, proteins and the anaerobic bacteria hiding in the crevices.

To summarize, in addition to physically removing the debris from the tongue, the invention presents a synergistic mechanism wherein the transducer is located in the tongue scraper head transmitting non-attenuated ultrasound pressure waves to the tongue, and/or the transducer's silver contact surface is exposed to be in intimate contact with the tongue, synergistically enhancing the non-attenuated high intensity ultrasound transmitted into the tongue with the antimicrobial properties of silver for the elimination and deactivation of the anaerobic bacteria residing in the folds of the tongue and the papillae.

BRIEF DESCRIPTION OF THE DRAWINGS

FIG. 1A shows a longitudinal cross section and a schematic of the invention consisting of the tongue scraper head portion incorporating the scraping edge and the ultrasound transducer, and the handle portion containing the driving motor, electronic controls and a battery.

FIG. 1B shows a bottom view of the invention.

FIG. 2 shows the cross section of a removable tongue scraper head portion having an exposed non-attenuated ultrasound transducer.

DESCRIPTION OF THE PREFERRED EMBODIMENTS

Figure 3:
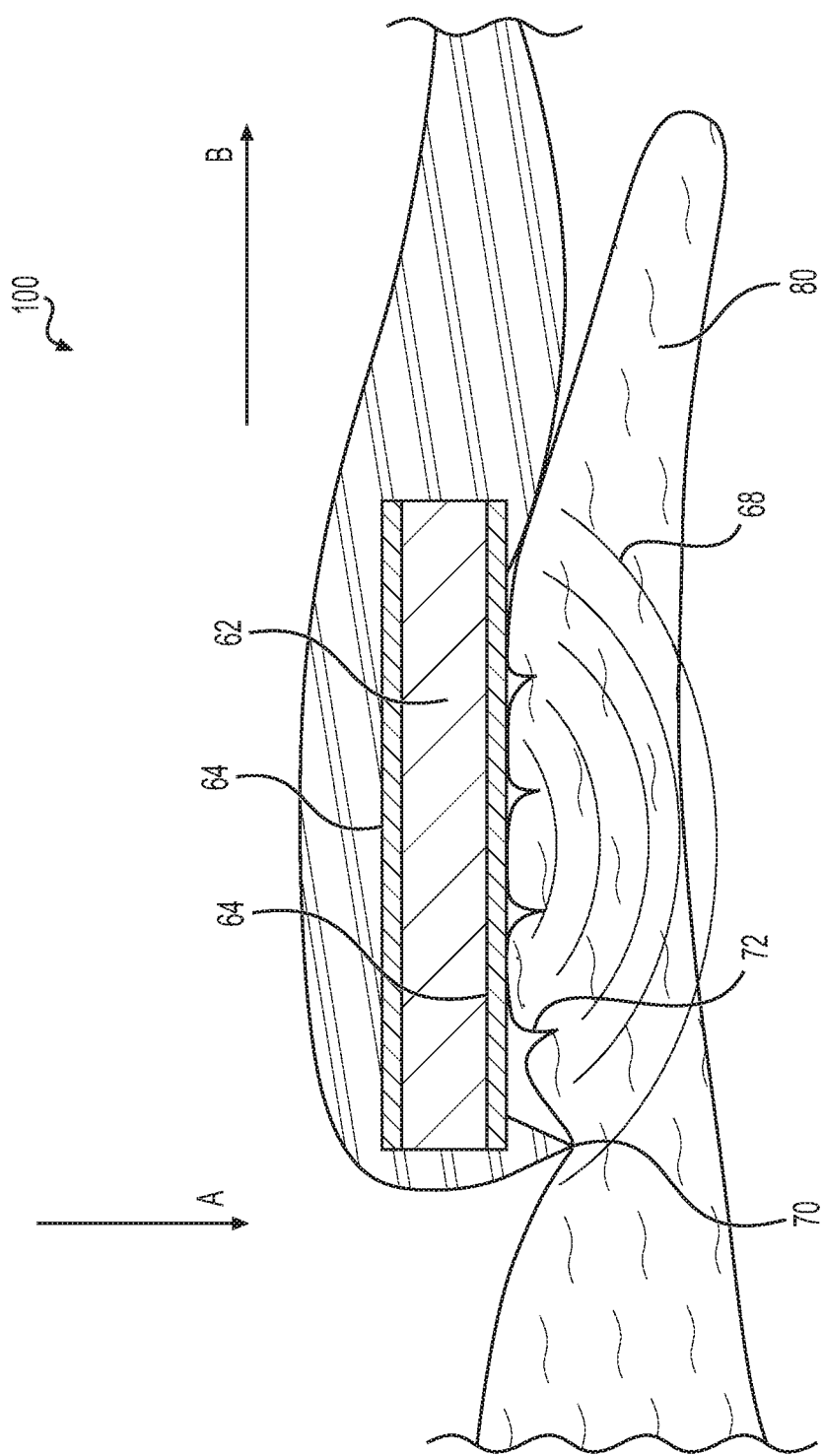
FIG. 3 shows a synergistic method of disabling and deactivating the anaerobic bacteria residing in the folds of the tongue.

The term "ultrasound" and "ultrasonic" and "ultrasonic pressure waves" refer to acoustic energy in either continuous wave ultrasound or repetitive burst type ultrasonic modality having an operating frequency of 20 kHz and above. References made to "sonic" and "sonic or sonic frequency vibrations" are referring to physical vibrations or oscillating motions significantly below the 20 kHz ultrasonic threshold, typically in the range of 100 to 500 Hertz. The term "cavitation" in association with the tongue scraper refers to the generation and/or dispersion of bubbles and the interaction between the sonic or ultrasonic energy and vibrations with the bubbles within the oral fluidic environment. The term "structural attenuation" in association with ultrasound refers to the attenuation effects of the various surface interfaces, air-gaps, and materials commonly used for housing ultrasound transducers in the process of transmitting ultrasound from the ultrasound generating transducer through the other parts of the device to the application surface in touch with the anatomy of the ultrasonic applications.

The damaging effects of ultrasound on bacteria and bacterial colonies and rendering bacterial colonies ineffective are well known and documented in the scientific community. It is well known that the effectiveness of ultrasound is related to the intensity of the application, so it is important to limit energy losses and maximize the available intensity from an ultrasound transducer within the limitation of the tissue-heating threshold.

The invention of the Improved Intensity Ultrasonic Tongue Scraper 20 in a preferred configuration is shown in FIG. 1A and FIG. 1B. The tongue scraper 20 comprises of a handle portion 30 and a tongue scraper head portion 60 typically constructed of a rigid or semi rigid plastic material.

The handle portion 30 typically contains a battery pack 36, an electronic control module 34, and an electric motor 32 with an off-center weight 33 mounted on the shaft of the motor 32. The battery pack 36 is typically a multi-cell rechargeable battery of NiCd or NiMH chemistry system providing approximately 4.8 VDC to the electronic control module 34. However, single cell as low as 1.2 VDC and non-rechargeable batteries could also be utilized in the construction of the device. The electronic control module 34 has multiple functions which are selectively activated by the multi function switch 40. The electronic control module 34 controls the electric motor 32 to produce various speed sonic frequency orbital vibrations 44 typically between 100 Hz and 500 Hz to the preference of the user, or no vibration when the user does not desire it. The electronic control module 34 generally will boost the battery voltage by a voltage multiplier circuit to the range of 9.6 VDC to 16.0 VDC in conjunction with generating the ultrasonic frequency current between 20 kHz and 20 MHz frequency, more typically within 750 kHz and 2 MHz frequency, for energizing the ultrasound transducer 62 through connective wiring 38 and contact pins 42B.

The tongue scraper head portion 60 features a scraping edge 70 and houses the ultrasound transducer 62. The ultrasound transducer 62 generally having silver plated contact surfaces 64 to which the connective wiring 66 is soldered to, terminating at the receptacles 42A.

The transducer 62 is typically constructed of one or more elements of hard piezo-electric materials, such as PZT-4 or PZT-8 Lead Zirconate Titanate composition ceramics. The PZT-8 material is a particularly good candidate for the tongue cleaner application since it is capable of producing large mechanical drive amplitudes while maintaining low mechanical and dielectric losses. However various other transducer materials are also available in the art, such as single crystal silicones, capacitive micro-machined materials, electrostatic polymers, and more will be available in the future to construct an ultrasonic transducer. When energized by the ultrasonic frequency current supplied by the electronic control module 34 trough the interconnecting wiring 38, pins 42B, receptacles 42A and wiring 66, the transducer 62 expands and contracts in tune with the ultrasonic frequency current, producing and transmitting ultrasound pressure waves 68 through the ¼ wave ultrasound matching layer 69 into the tongue as further depicted in FIG. 3.

FIG. 2 depicts another configuration of the tongue scraper head 100. On the scraping edge 70 side of the tongue scraper head 100 the majority of the silver plated contact surface 64 of the transducer 62 is exposed to be in intimate contact with the tongue. The silver contact surface 64 can be enhanced with the infusion of silver nanoparticles. Scientific experiments with silver nanoparticles in sizes of 7-nm, 29-nm, 89-nm have shown that while all particle sizes were effective, smaller nanoparticles have more of an inhibitory effect on bacterial colonies than larger nanoparticles. In addition, the saliva moisture on the tongue further activates the silver particles to release silver ions (Ag+), which further enhances the antimicrobial properties of the silver contact surface 64.

Items 42A, 66, and 68 of FIG. 2 are having common functionality with same numbered items and described in FIG. 1.

FIG. 3 depicts the synergistic method of disabling and deactivating the anaerobic bacteria residing in the folds 72 of the tongue 80 by the simultaneous application of ultrasonic pressure waves 68 and the antimicrobial properties of the silver contact surface 64 of the ultrasound transducer 62. First the user flushes the scraping edge 70 side of the scraper head 100 and the exposed ultrasound transducer 62 with water and activates the ultrasonic pressure waves 68 by the control switch 40 (shown in FIG. 1A), then brings the scraping edge 70 side of the scraper head 100 into contact with the tongue 80. The user then presses down on the scraper head 100 in the direction A until the silver contact surface 64 comes into contact with the tongue 80 and the scraping edge 70 bites into and stretches the top surface of tongue 80. At that moment of contact the moisture of the saliva further enhances the coupling of the ultrasonic pressure waves 68 into the tongue 80 and enhances the Ag+ ion release from the silver contact surface 64.

The user then pulls the scraper head 100 toward the front of the tongue 80 in the direction B scraping off any debris from the tongue 80 and progressively irradiating the entire surface and the folds 72 and the papillae of the tongue 80 with high intensity ultrasonic pressure waves 68 and Ag+ ions from the silver contact surface 64.

All of the patents and publications cited herein and in the appended Information Disclosure Statement are hereby incorporated by reference in their entireties.

The expressions of "ultrasound" and "ultrasonic" are used interchangeably. The expressions of "typical", "typically", "usually" etc. does not exclude other components, materials, and methods, merely present some more frequently used alternatives.

While the preceding description contains much specificity, these should not be construed as limitations on the scope of the invention, but rather as an exemplification of some preferred embodiments among the many additional embodiments thereof. Skilled artisans will readily be able to change dimensions, shapes, and construction materials of the various components described in the embodiments and adopt the invention to all types of sonic and ultrasonic energy applications. Accordingly, the scope of the invention should be determined not by the embodiments illustrated, but by the appended claims and their legal equivalents.

What is claimed:

1. An ultrasonic tongue cleaner comprising:
   a) a tongue cleaner head portion having at least one scraping edge extending perpendicularly from a tongue contacting surface of said tongue cleaner head portion and configured for pushing into and stretching a top surface of said tongue, and configured for enhancing coupling of a non-attenuated ultrasound pressure waves into said top surface of said tongue and scraping off debris from said tongue and at least one ultrasound transducer inside said cleaning head portion, said ultrasound transducer configured for radiating and coupling said non-attenuated ultrasound pressure waves into said tongue to impact bacteria residing on said top surface and in folds of said tongue;
   b) a handle portion containing means generating ultrasonic frequency electronic current and connecting means of said electronic current to energize said ultrasound transducer located in said tongue cleaner head portion.

2. The ultrasonic tongue cleaner of claim 1, wherein the ultrasonic pressure waves radiated by said transducer are non attenuated and operating between 20 kHz and 20 MHz frequency and producing non attenuated ultrasound intensity of 0.02 to 0.5 W/cm$^2$.

3. The ultrasonic tongue cleaner of claim 1 or 2, wherein the said ultrasound pressure waves radiated by said transducer are operative to damage and reduce the effectiveness of odor causing bacteria and bacterial colonies on the surface and in the folds of the tongue.

4. The ultrasonic tongue cleaner of claim 1 or 2, wherein said tongue cleaner head portion is removable from said handle portion and includes means to securely connect said tongue cleaner head portion to said handle portion and means to connect said ultrasonic frequency electronic current from said handle portion to power said ultrasound transducer within said tongue cleaner head portion.

5. The ultrasonic tongue cleaner of claim 1 or 2, additionally comprising a motor secured to the structure of said handle portion having means to generate orbital vibrations of said handle portion and said tongue cleaner head portion.

6. The ultrasonic tongue cleaner of claim 5, wherein the frequency of said orbital vibrations is between 100 Hz and 500 Hz.

7. The ultrasonic tongue cleaner of claim 5, further comprising means to selectively generate orbital vibrations or not to generate said orbital vibrations of said handle portion and said tongue cleaner head portion according to the desires of the user.

8. The ultrasonic tongue cleaner of claim 5, wherein said tongue cleaner head portion is removable from said handle portion and includes means to securely connect said tongue cleaner head portion to said handle portion having means to transmit said orbital vibrations from said handle portion to said removable tongue cleaner head portion and means to connect said ultrasonic frequency electronic current from said handle portion to power said ultrasound transducer within said tongue cleaner head portion.

\* \* \* \* \*